(12) United States Patent
Consolaro et al.

(10) Patent No.: US 11,638,783 B2
(45) Date of Patent: May 2, 2023

(54) OPENING AND SUPPLYING SYSTEM FOR PRE-FILLED CONTAINERS, RESPECTIVE FILLED CONTAINERS, AND METHODS FOR THEIR REALIZATION

(71) Applicant: Brevetti Angela S.r.l., Arzignano (IT)

(72) Inventors: Roberto Consolaro, Arzignano (IT); Angelo Consolaro, Arzignano (IT); Rajeev Virbhadra Kabbur, Arzignano (IT)

(73) Assignee: Brevetti Angela S.r.l., Arzignano (IT)

( * ) Notice: Subject to any disclaimer, the term of this patent is extended or adjusted under 35 U.S.C. 154(b) by 1242 days.

(21) Appl. No.: 16/079,102

(22) PCT Filed: Feb. 23, 2017

(86) PCT No.: PCT/IT2017/000034
§ 371 (c)(1),
(2) Date: Aug. 23, 2018

(87) PCT Pub. No.: WO2017/145188
PCT Pub. Date: Aug. 31, 2017

(65) Prior Publication Data
US 2019/0060573 A1    Feb. 28, 2019

(30) Foreign Application Priority Data

Feb. 23, 2016   (IT) .................. 102016000018646

(51) Int. Cl.
*A61M 5/28*   (2006.01)
*A61M 5/34*   (2006.01)
(Continued)

(52) U.S. Cl.
CPC .............. *A61M 5/288* (2013.01); *A61M 5/24* (2013.01); *A61M 5/34* (2013.01); *A61M 39/10* (2013.01);
(Continued)

(58) Field of Classification Search
CPC .......... A61M 5/288; A61M 5/24; A61M 5/34; A61M 39/10; A61M 5/282; A61M 5/345;
(Continued)

(56) References Cited

U.S. PATENT DOCUMENTS

| 2,671,449 A | 3/1954 | Dann |
| 2,671,450 A | 3/1954 | Dann |
| 4,740,205 A * | 4/1988 | Seltzer ............. A61B 5/150587 604/192 |

FOREIGN PATENT DOCUMENTS

| WO | WO 2007/089531 | 8/2007 |
| WO | WO 2017/145188 | 8/2017 |

OTHER PUBLICATIONS

International Search Report and the Written Opinion dated Jun. 9, 2017 From the International Searching Authority Re. Application No. PCT/1T2017/000034. (11 Pages).

(Continued)

*Primary Examiner* — Amber R Stiles

(57) ABSTRACT

The present invention relates to an opening and liquid supplying system (100) for pre-filled containers (10, 30) equipped with a supplying end, comprising a coupling element (20), connecting means (6) movable from a first position to a second position, and movable protection means (9); the coupling element (20) has an end (27) closed and suitable for being punched, and first guiding means (21) for guiding the movement of the connecting means (6) movable from the first position, close to the closed end (27), to the second position, apart from such end, and vice versa; the connecting means (6) have engaging means (7) for engaging with the protection means (9) so as to move integrally along a second degree of freedom, different than the first degree of freedom, and first matches (11) for the first guiding means (21).

(Continued)

The invention relates also to a respective pre-filled container equipped with such system and the method for realize them.

6 Claims, 3 Drawing Sheets

(51) Int. Cl.
    *A61M 5/24*     (2006.01)
    *A61M 39/10*     (2006.01)
    *B29C 65/56*     (2006.01)
    *B29C 49/04*     (2006.01)
    *A61M 39/18*     (2006.01)

(52) U.S. Cl.
    CPC ........... *B29C 65/561* (2013.01); *A61M 5/282* (2013.01); *A61M 5/345* (2013.01); *A61M 5/346* (2013.01); *A61M 39/18* (2013.01); *A61M 2005/2444* (2013.01); *A61M 2207/00* (2013.01); *B29C 49/04* (2013.01)

(58) Field of Classification Search
    CPC ................ A61M 5/346; A61M 39/18; A61M 2005/2444; A61M 2207/00; A61M 5/2455; A61M 2005/3103; B29C 65/561; B29C 49/04; A61J 1/06
    See application file for complete search history.

(56) References Cited

OTHER PUBLICATIONS

Rapporto di Ricerca e Opinione Scritta [Search Report and Written Opinion] dated Oct. 28, 2016 From the Ministero dello Sviluppo Economico. Direzione Generale Sviluppo Produttivo e Competitivita Uffico Italiano Brevetti e Marchi Re. Application No. ITUB20160977. (7 Pages).

\* cited by examiner

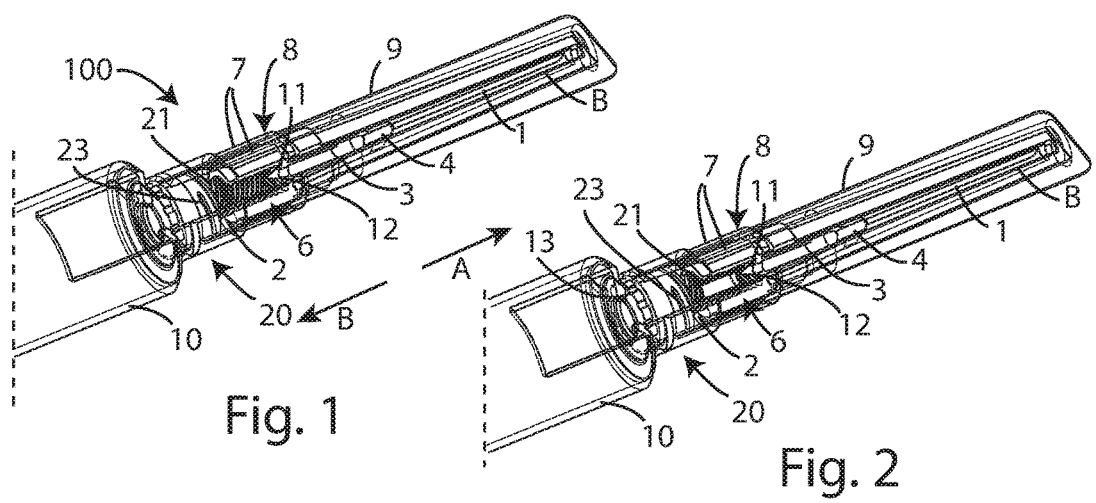
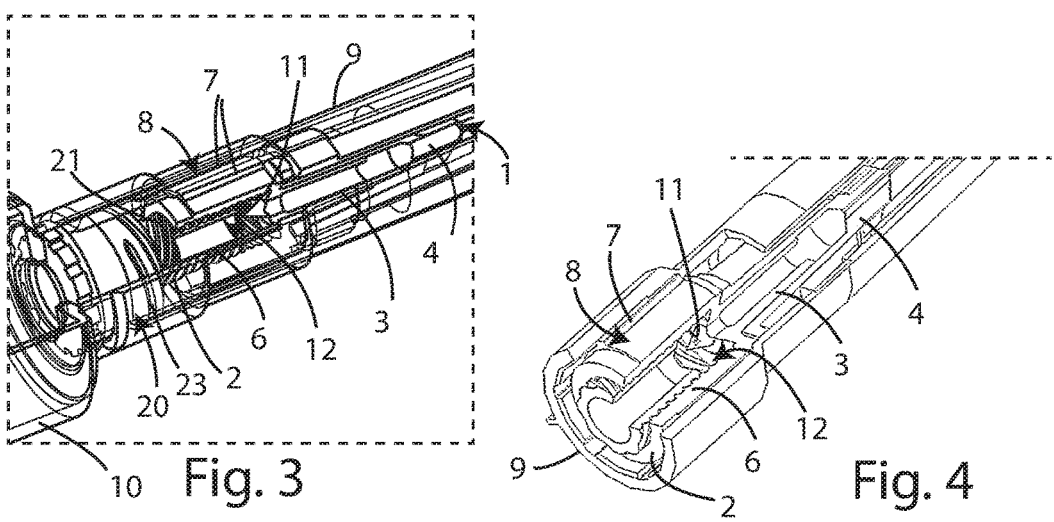
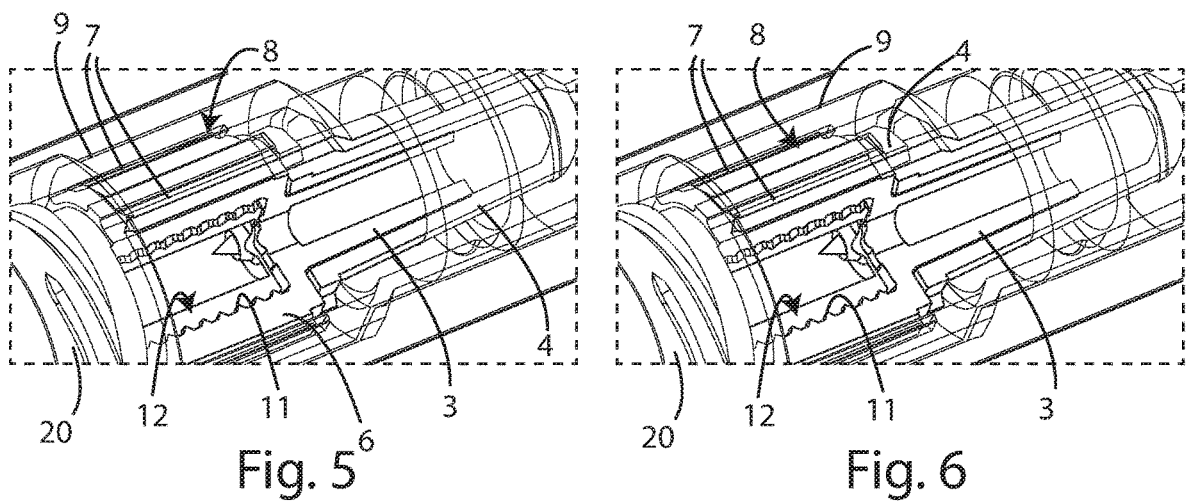

OPENING AND SUPPLYING SYSTEM FOR PRE-FILLED CONTAINERS, RESPECTIVE FILLED CONTAINERS, AND METHODS FOR THEIR REALIZATION

The present invention relates to an opening and supplying system for pre-filled containers. In detail, the invention relates to an opening system for pre-filled syringes or vials which allows keeping the needle apart from the medicament until the moment when it is actually used.

In the syringes which are pre-filled with a given medicament, the same medicament stays inside the syringe for long periods.

Some medicaments are not compatible with the material, of which the needle is made up, and may lose effectiveness or even become harmful, while sometimes their formulation may generate residues which may obstruct the needle, preventing—at the moment of use—the liquid to leak out from the syringe.

Object of the invention is removing this problem, making the syringe usable by the user at any time, by a simple action.

A method for producing syringes is known, from the patent n. WO2011001456. Such method, which describes an application of the technique named BLOW FILL SEAL or BFS (shown in the patents WO2007007178 and WO2010143219) requires that the airtight closure (or seal: Seal step) occurs forming a cap or another closing element connected to the hollow body of the container and movable by means of an area having a thinner section, facilitated breakage.

Furthermore, pre-filled syringes placed within an outer wrap in order to keep them sterile until the moment of use are known.

Nevertheless, the cap or the wrap which cover the stem or the whole syringe have the drawback of being expensive during production of the syringe, since it requires an extra use of plastics.

As a consequence, in case of large scale production, the use of plastics for producing the syringe, the dimension of the stem to be sterilized and subsequently stocked and managed in the assembly lines, as well as their subsequent disposal, make the syringe ecologically and economically unsustainable.

Above all, such method does not solve the drawback lamented above of the risk of contamination of the medical liquid by the needle.

A vial or syringe produced by the mentioned above method BFS or other methods exists, too, which provides using an accessory comprising a needle embedded in a threaded ring equipped with a protecting cover for the needle: while the component screws, with the inner part of the needle, a membrane on the vial or syringe is perforated, putting in communication the medicament or liquid to be injected, contained in the vial or in the syringe, so as to make them ready to use.

Nevertheless, such accessory is not easily obtainable on the market, nor it is easy to be realized.

Furthermore, often such accessory is not completely reliable, with the risk of compromising the operation to be executed or the safety of the user who has to handle the vial or the syringe.

There is therefore the need of a closing system for pre-filled syringes which allows the containing and the conservation of a substance, which is easy to be opened by a user, respects the required specifications by the operator, but which at the same time keeps unchanged its content over time.

The present invention is proposed to compensate for drawbacks of prior art just lamented.

In particular, main object of the invention is to develop an opening system for pre-filled syringes, a syringe equipped with such system and a method for its production and assembly which assures the same syringe the possibility to be usable by the user at any time, by a simple action.

In particular the invention has the aim of realizing an opening system for pre-filled syringes, a syringe equipped with such system and a method for its realization which allows keeping the needle apart from the medicament until the moment of use.

More in detail, the invention has the aim of realizing an opening system for pre-filled syringes, a syringe equipped with such system and a method for its realization which allows connecting the needle to the hollow body containing the medicament with the same opening operation.

Another object of the present invention is to devise an opening system for pre-filled syringes, a syringe equipped with such system and a method for its realization which, although assuring the achieving the purposes mentioned above, have an early implementation.

Further object of the invention is equipping an opening system for pre-filled syringes, a syringe equipped with such system and a method for its realization and assembly which guarantees a more practical use for the operator or for the devices to which it is applied.

Said objects are reached by an opening system for pre-filled syringes, a syringe equipped with such system and a method for its realization and assembly according to the attached independent claims 1 and 8, to which reference is made for brevity.

Further application features of the method of the invention are highlighted in the respective dependent claims.

Advantageously, the system of the invention allows setting up a container or a syringe for medical operations, even in its constructive basic manning, without any manipulation of the components of the same syringe by the user.

This allows for example making totally aseptic a syringe for medical operations and enabling, as a consequence, a subsequent use in optimal conditions of safety under the profile of hygiene and health of the people involved, patients and workers.

As much advantageously, this is reflected in a significant reduction of the cost of production of a syringe compared to the current state of the technique, of course, the other factors involved being equal.

In advantageous manner, furthermore, the syringe obtained with the system of the invention has functional properties at least equivalent to those of the known syringes with respect to which keeps, however, the above highlighted advantages.

In detail, the subject matter of the invention is an opening and liquid supplying system for pre-filled containers equipped with a supplying end, comprising a coupling element for coupling with the container, connecting means movable from a first position to a second position, and movable protection means.

Such connecting means are suitable for housing a needle holder, for example with a standard assembly or with an ad hoc assembly, or being realized integral with each other.

The coupling element has a first hollow end, suitable for coupling with the supplying end of the container, and a second closed end suitable for being punched; furthermore such coupling element has first guiding means for guiding the movement of the connecting means movable from the first position, close to the second end, to the second position, close to the first end, and vice versa along a first degree of freedom.

The connecting means have engaging means for engaging with the protection means so as to move integrally with each other along a second degree of freedom, different than the first degree of freedom, and first matches for the first guiding means; in such a way, advantageously, during the integral movement of the protection means and of the connecting means, the first matches of the connecting means move from the first position to the second position along the first guiding means of the coupling element.

This allows keeping the pre-filled container sealed, with the needle apart from its supplying end, preventing that the liquid inside the container is contaminated by the same needle, or that the same liquid creates obstructions inside the needle.

At the same time, advantageously, the system of the invention allows to make the pre-filled container immediately ready for use, without the operator is forced to handle aseptic elements prematurely.

Preferably, according to the invention, the connecting means are integral with a needle holder, equipped with a supplying needle, suitable for punch the second end of the coupling element, when the connecting means are in the second position.

Furthermore, according to the invention, the engaging means may comprise protruding elements suitable for sliding along longitudinal grooves on the inner surface of the protection means.

Still, according to the invention, the first guiding means may have limits, so as to, advantageously, allow easily operate on the protection means, so as to not risk breakages or obstructions of the channel.

As much advantageously, the coupling element may have second guiding means for guiding the removal of the protection means, while the protection means may have second matches corresponding to the second guiding means, so that the removal movement of the protection means corresponds to the movement of the protection means in respect with the connecting means.

In such a way, in fact, with a single obliged move removing the protection means from the pre-filled container and opening the same container is possible, making such operation intuitive for whomever.

In detail, the first guiding means of the coupling element may comprise a first thread, while the first matches of the connecting means may comprise a first counter thread, on an inner surface of the connecting means and corresponding to the first thread.

Advantageously, such configuration is easy to be realized during performing the method of forming the system, moulding the counter thread by the pressure of the connecting means when they are still hot on the threaded surface of the coupling element, so as to shorten the production time of the same system.

In such case, the second guiding means of the coupling element may also comprise a second thread, with a direction opposite to the one of the first thread, while the second matches of the protection means may comprise a second counter thread, on an inner surface of the protection means and corresponding to the second thread.

Advantageously, such guiding means are easy to be realized, during the method of production, on the above explained principle; furthermore, such guiding means are also very easy to be used by whoever, making even more effortless the operation of opening the pre-filled container.

In other words, for the operator unscrewing the protection means is enough (for example, a cap), for activating the movement of the connecting means along the coupling element, bringing the needle to punch the closed end of the coupling element: once the protection means are removed, the pre-filled container is ready to supply the liquid contained within it.

The invention relates furthermore to a pre-filled container for supplying liquids, for example medical liquids, which comprises an opening and supplying system according to the invention.

Said aims and advantages, as well as others which will arise in the following, will be more apparent from the following description relating to a favourite embodiment of the system of the invention, given by way of example and illustrative, but not limitative, with reference to the accompanying drawings in which:

FIG. 1 shows a first cutaway of the closing system of the invention in a first position, applied to a syringe;

FIG. 2 shows the cutaway of the system of FIG. 1 wherein the components are seen in transparency;

FIG. 3 shows a detail of FIG. 2;

FIG. 4 shows a second cutaway of the system of FIG. 1, removed from the syringe;

FIG. 5 shows a cutaway of the system of FIG. 1, in a second position;

FIG. 6 shows a detail of FIG. 5;

Figure 12:
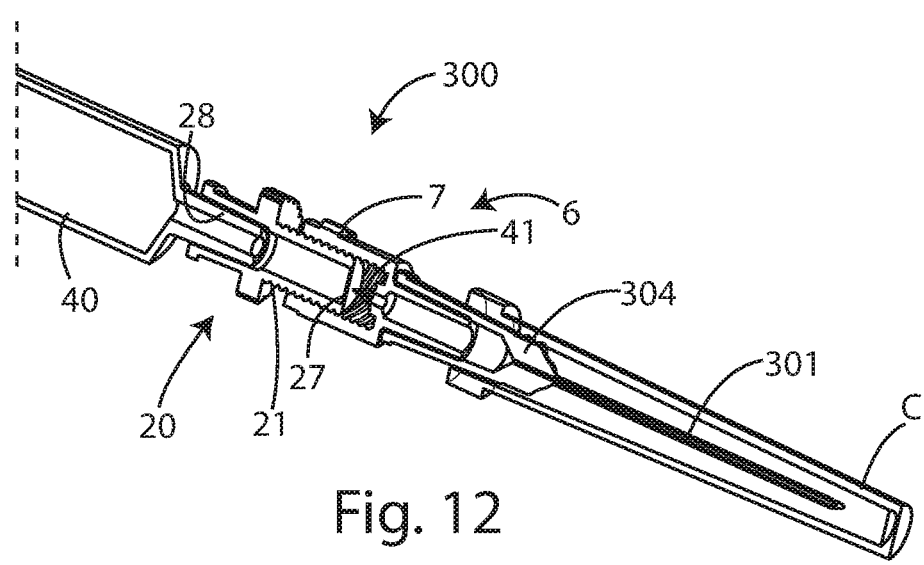
FIG. 12 shows in cross section the system of FIG. 11, in a first position, before punching.
Figure 13:
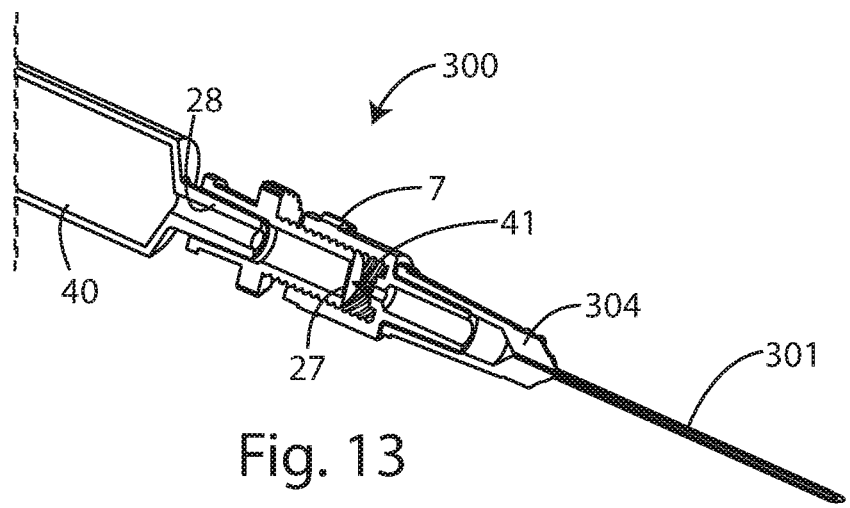

FIG. 13 shows in cross section the system of FIG. 12, in a second position, with the needle in communication with the liquid, ready to use. Referring to FIGS. 1-6, the opening system 100 for pre-filled syringes 10 of the invention comprises connecting means 6, equipped with a first end 2 for sampling of the medical liquid from a connector 20 suitable for being punched, and equipped with a second end 3 suitable for being connected to a needle 1 for supplying the medical liquid.

The needle 1 is held by a needle holder element 4, and by connecting means (for example Luer) for being connected to the connecting means 6, in turn assembled with the connector 20, and to be coupled to the syringe 10.

The connecting means 6 are integral to the needle holder 4 according to the prior art (for example, by a Luer connection) and have: engaging means 7, for example at least a longitudinal rib, on at least a portion of the coupling surface 8 with protection means 9 of the needle 1, for example a cap 9.

The system 100 comprises furthermore a connector or coupling element 20, suitable for coupling the container of medical liquid, for example the pre-filled syringe 10 realized by the BFS technique, by the connecting means 6 with the needle holder 4.

Figure 7:
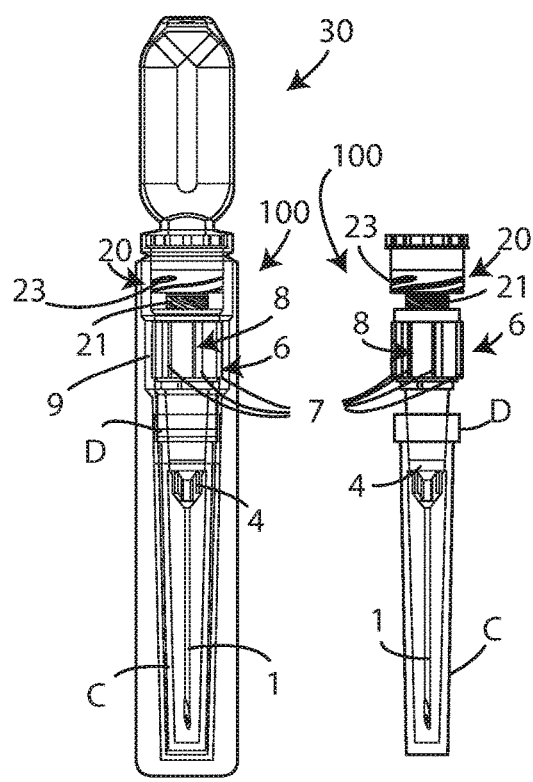
FIG. 7 shows the system of the invention in a first variant, wherein it is applied to a vial.

Furthermore, the needle guard C is coupled to the cap 9, for example embedding the needle guard C into the cap 9 when the cap 9 is still hot and thus malleable; in particular this could occur embedding exclusively the base portion D of the needle guard C (FIG. 7, 9, 10).

The coupling element 20 has guiding means 21, corresponding to the first matches 11 on at least a surface 12 of the connecting means 6.

In particular, for example, the coupling element 20 has a substantially tubular shape, the cavity of which is coupled to the supplying end of the container (for example embeds the supplying end of the pre-filled syringe 10, in particular this may occur coupling the coupling element when is still hot and thus malleable), while its external surface has a thread 21, corresponding to a counter thread on the inner surface 12 of the connecting means 6 of the needle holder 4.

Preferably, the coupling element 20 has a limit of the guiding means 21, for the first matches 11 of the connecting means 6 of the needle holder 4.

As much preferably, a portion of the coupling element 20 has guiding means 23 for the first matches 13 of the cap 9, for example a thread 23 and a counter thread 13, with a direction opposite to the one of the thread 21 and of the counter thread, so that, when the operator rotates the cap 9 clockwise, this is guided along a first direction A, corresponding to the moving away of the cap 9 from the rest of the system 100, while the connecting means 6 with the needle holder 4, as above explain, are guided along a second direction B, opposed to the first direction A.

In a first variant of the invention, shown in FIG. 7, the opening system 100 of the invention is applied to a vial 30, for example realized always with BFS technology, in particular of the squeeze type.

The connecting means 6 of the system 100 have substantially a tubular shape, suitable for housing within it a part of the coupling element 20, and on the external surface of which there is at least a protruding element or a longitudinal rib, suitable for engage with at least a corresponding seat or longitudinal groove (not shown) on the inner surface of the cap 9 for protecting the needle 1, so that—rotating the cap 9 in order to remove it from the needle 1—the needle holder 4 rotates according to the same direction of the same cap.

Even if in the attached drawings they are always shown in such way, it is not necessary that the engaging means 7 are placed in correspondence of the connecting means 6, but they must surely be placed so as to engage with the inner surface of the cap 9.

Figure 8:
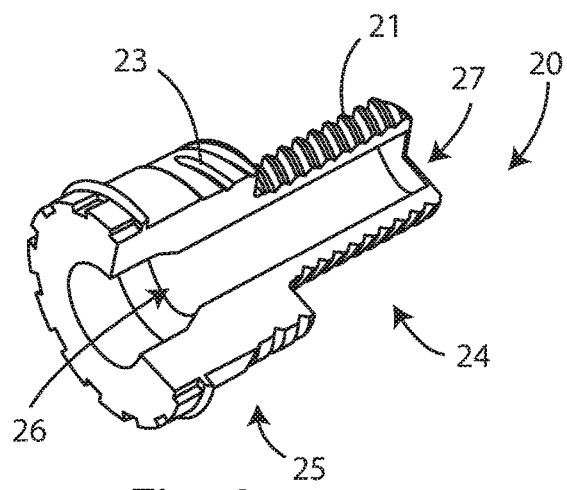
FIG. 8 shows a component of the system of FIG. 7.
Figure 9:
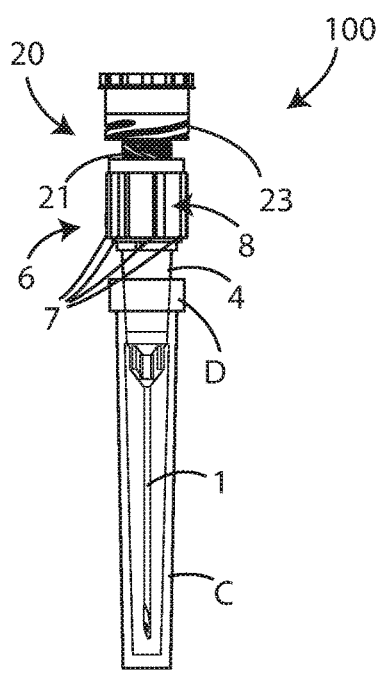
FIG. 9 shows the system of the invention to which a standard needle is applied.
Figure 10:
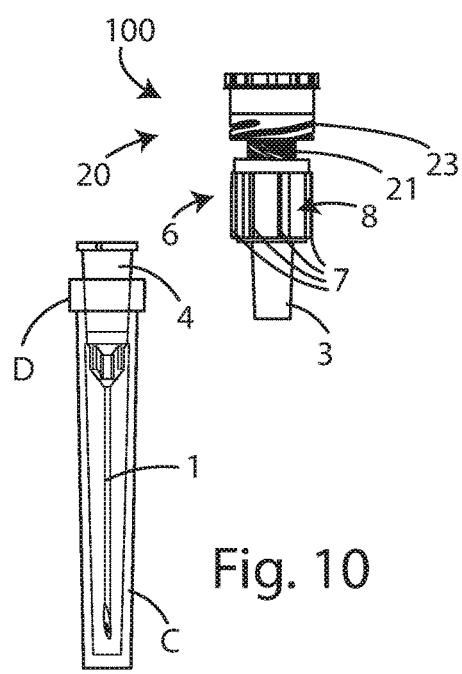
FIG. 10 shows an exploded view of FIG. 9.

The coupling element 20, shown in FIG. 8, has a hollow volume composed substantially by a first hollow cylinder 24, equipped with a first external diameter, and preferably also by a second hollow cylinder 25, equipped with a second external diameter, bigger than the first.

On the first cylinder 24, there are guiding means 21, in the example shown in FIG. 8 a thread having a first direction, to which a counter thread on an inner surface 12 of the connecting means 6 of the needle holder 4 corresponds.

The first cylinder 24 has a first end, hollow, 26 suitable for facing to towards the supplying end of the container 10 or 30, and a second end 27, closed.

The second hollow cylinder 25 acts as a limit for the thread 21 for the connecting means 6.

Furthermore, preferably, the second hollow cylinder 25 has on its external surface a further thread 23, having a second direction, opposed to the first, to which a second counter thread 13 on the inner surface of the cap 9 corresponds.

Figure 11:
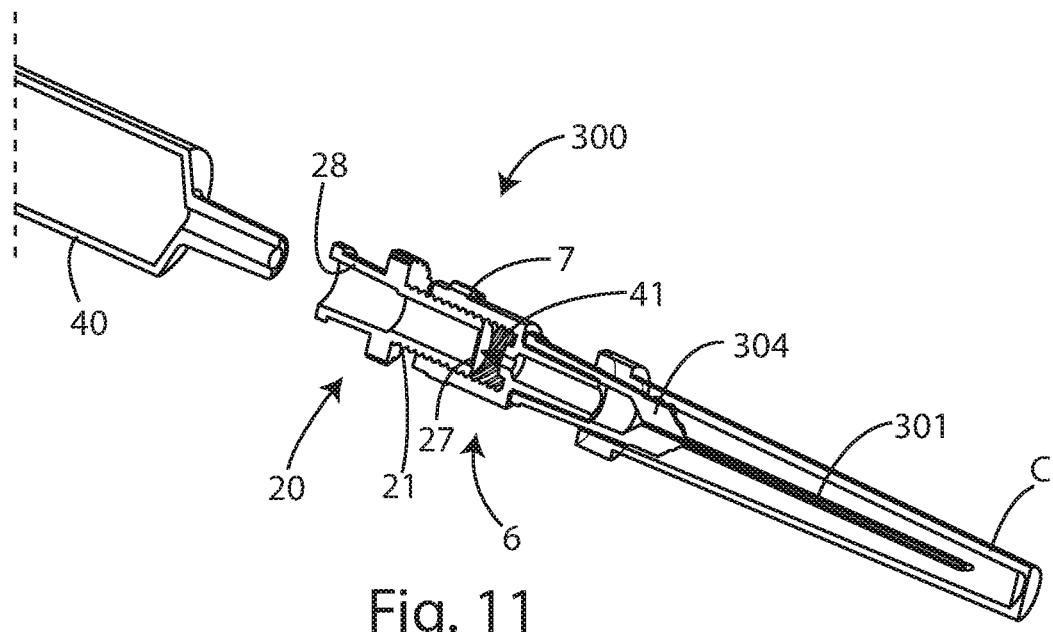
FIG. 11 shows an exploded view in cross section of FIG. 9 applied to a standard syringe.

As shown in the variant of FIGS. 11-13, the system 300 of the invention may be suitable for be applied to a syringe 40 standard, for example with a LUER connection.

In such case, the system 300 of the invention comprises only connecting means 6 and a modified coupling element 20, i.e. having the inner surface 28 with Luer connection for being coupled into the known system to the standard syringe 40.

In particular, the connecting means 6 have the same elements already described for the system 100.

The engaging means 7 are rotated by the operator and following the thread of the guiding means 21 on the coupling element 20, as already described, punch the closed end 27 by means of the inner end 41 of the needle 1 creating the connection of the liquid within the syringe with the standard needle connected by a Luer connection.

During the assembly and packaging of the container (visible in FIG. 12), a needle 301 equipped with a needle holder 304 with a standard connection, for example a Luer connection, is added.

Operationally, however, when the operator takes a container 10 or 30 or 40 containing the medical liquid to which is applied the opening system 100 or 300 of the invention, such system 100 or 300 is in a first position, with the connecting means 6 apart from the supplying end of the container 10, 30 or 40 (FIGS. 1-3 and 12).

During opening step, the operator acts on the cap 9, if on the container, or directly on the lugs 7 (FIGS. 12 and 13), rotating along a rotational direction, for example along a clockwise direction. In this way, the cap 9 starts rotating, engaging with the engaging means 7 of the connecting means 6. In such a way, the connecting means 6 start rotating in the same direction: in this case, clockwise. During the rotation of the connecting means 6, it is guided by the first matches 11 along the path set by the guiding means 21 of the coupling element 20 towards the supplying end of the container 10 or 30 or 40, up to punch the second end 27 of the supplying element 20 with the first end 41 of the connecting means 6 and arrive in a second position, wherein the needle 1 or 301 gets in communication with inside the container 10 (FIGS. 5, 6 and 13) for supplying.

Meanwhile, also the connecting means 6 longitudinally moved towards such supplying end of the container 10, 30 or 40.

In such a way, the container 10 or 30 is free from the cap 9 and from the possible needle guard C, ready to be used, with the needle 1 or 301 in contact for the first time with the medical liquid.

From the description just made, it is clear, thus, that the opening system of the invention, the pre-filled container and the method for its production and assembly, subject matter of the present invention, reach the objects and realize the advantages already mentioned.

During the execution, changes to the components of the system of the invention may be made, consisting, for example, in inverting the position of the guiding means and of the respective first matches with each other.

In such case, the procedures described above for realizing the system of the invention will vary accordingly.

It is clarified, moreover, that the present invention, although having been described with particular reference to a pre-filled single use syringe and a vial for injections, extends also to others liquid containers.

It is clear that many other variations may be made to the system in question, without for this departing from the principles of novelty inherent in the inventive idea expressed here, it is also clear that, in the practical implementation of the invention, the materials, the shapes and dimensions of the illustrated details can be whatever, depending on the requirements, and replaced by others technically equivalent.

Where the constructive and technical characteristics mentioned in the subsequent claims are followed by signs or reference numbers, such reference signs have been introduced with the sole aim of increasing the intelligibility of the same claims and, as a consequence, they have no limiting effect on the interpretation of each element identified by way purely of example, by such reference signs.

What is claimed is:

1. A method for the realization of an opening and liquid supplying system (100) for containers (10, 30) equipped with a supplying end, comprising a coupling element (20), connecting means (6) movable from a first position to a second position, and movable protection means (9), the connecting means (6) being suitable for coupling with a needle holder (4) comprising the following steps:

provipding in the coupling element (20) a first hollow end (26), suitable for coupling with the supplying end of the container (10, 30), and a second end (27), closed and suitable for being punched;

providing on the coupling element (20) a first guiding means (21) for guiding the movement of the connecting means (6) movable from the first position, close to the second end (27), to the second position, close to the first hollow end (26), and vice versa along a first degree of freedom;

providing on the connecting means (6) an engaging means for engaging with the protection means (9) so as to integrally move along a second degree of freedom, different than the first degree of freedom, and first matches for the first guiding means (21), so as, during the integral movement of the protection means (9) and of the connecting means (6) according to the second degree of freedom, the first matches of the connecting means (6) move from the first position to the second position along the first guiding means (21) of the coupling element (20);

providing on the coupling element (20) a second guiding means (23) for guiding the removal of the protection means (9); and providing on the protection means (9) second matches (13) corresponding to the second guiding means (23), so that the removal movement of the protection means (9) corresponds to the movement of the protection means (9) in respect with the connecting means (6);

making the container, the protection means or the coupling element malleable;

wherein the coupling of the coupling element (20) with at least one among the container (10, 30), the protection means (9) and the connecting means (6), occurs when the container (10, 30), the protection means (9) or the coupling element (20) is still malleable;

wherein the first guiding means of the coupling element (20) comprise a first thread, and wherein the first matches of the connecting means (6) comprise a first counter thread, on an inner surface (12) of the connecting means (6) and corresponding to the first thread;

wherein the second guiding means of the coupling element (20) comprise a second thread, with a direction opposite to the one of the first thread and wherein the second matches of the protection means (9) comprise a second counter thread (13), on an inner surface of the protection means (9) and corresponding to the second thread;

wherein at least one among the first counter thread and the second counter thread (13) is realized by pressing respectively the connecting means (6) and the protection means on the coupling element (20) while the connecting means (6) and the protection means (9) are still malleable.

2. The method for the realization of an opening and liquid supplying system (100) according to claim 1, further comprising the following steps:

providing the connecting means (6) integral with a needle holder (4) equipped with needle (1) suitable for punching the second end (27) of the coupling element (20), when the connecting means (6) are in the second position;

providing a needle guard (C) for the needle holder (4), embedding at least a portion of the needle guard (C) in the protection means (9) whene protection means (9) is still malleable.

3. The method for the realization of an opening and liquid supplying system (100) according to claim 1, wherein the first guiding means are realized by pressing the connecting means (6) while still malleable on the coupling element (20).

4. The method for the realization of an opening and liquid supplying system (100) according to claim 1, further comprising the following step:

realizing the second guiding means of the coupling element (20) by pressing the protection means (9) while still malleable on the coupling element (20).

5. The method for the realization of comprising an opening and liquid supplying system (100) according to the method of claim 1 further comprising a pre-filled container (10, 30).

6. The method according to the claim 5, further comprising the following step:

embedding the supplying end of the container (10, 30) in the coupling element (20) when the coupling element (20) is still malleable.

* * * * *